(12) United States Patent
Moseley et al.

(10) Patent No.: US 7,628,957 B1
(45) Date of Patent: Dec. 8, 2009

(54) CARBON DIOXIDE SENSOR

(76) Inventors: Patrick T. Moseley, ILZRO, 2525 Meridian Pkwy., Durham, NC (US) 27713; Odile Merdrignac-Conanec, ILZRO, 2525 Meridian Pkwy., Durham, NC (US) 27713; Ronan Lebullenger, ILZRO, 2525 Meridian Pkwy., Durham, NC (US) 27713

( * ) Notice: Subject to any disclaimer, the term of this patent is extended or adjusted under 35 U.S.C. 154(b) by 222 days.

(21) Appl. No.: 11/475,839

(22) Filed: Jun. 27, 2006

Related U.S. Application Data

(60) Provisional application No. 60/694,344, filed on Jun. 27, 2005.

(51) Int. Cl.
*G01N 27/00* (2006.01)
(52) U.S. Cl. .................................. 422/82.01
(58) Field of Classification Search ............... 422/82.01
See application file for complete search history.

(56) References Cited

U.S. PATENT DOCUMENTS 1,625,925 A * 4/1927 Bloomfield et al. ......... 518/714
4,542,640 A * 9/1985 Clifford ..................... 73/31.06
6,173,201 B1 * 1/2001 Front ......................... 600/429

FOREIGN PATENT DOCUMENTS

GB         2166244 A  *  4/1986

OTHER PUBLICATIONS

Morimoto, T.; Muraishi, H. "Determination of heat of chemisoprtion of carbon dioixde on zinc oxide by means of surface reaction chemistry." J. Phys. Chem. 1976, 80(17), pp. 1876-1878.*
Williams, D.E.; Moseley, P.T. "Dopant Effects on the Response of Gas-Sensitive Resistors Utilising Semiconducting Oxides." J. Mater. Chem. 1991, 1(5), pp. 809-814.*

* cited by examiner

*Primary Examiner*—Walter D Griffin
*Assistant Examiner*—Bobby Ramdhanie
(74) *Attorney, Agent, or Firm*—James Creighton Wray; Meera P. Narasimhan

(57) ABSTRACT

A sensor responds sensitively to low concentrations of carbon dioxide in an atmosphere of air. Carbonates formed at the surface of preferred oxides can be decomposed by raising the temperature, thus reforming the original oxide. A $CO_2$ sensor operating according to this principle may be cycled between the temperature at which the surface carbonate is decomposed and the temperature at which the surface carbonate is formed from atmospheric carbon dioxide. The present invention relates to sensors and more particularly to sensors suitable for use in gaseous mixtures containing carbon dioxide.

2 Claims, 4 Drawing Sheets

CARBON DIOXIDE SENSOR

This application claims the benefit of U.S. Provisional Application No. 60/694,344, filed Jun. 27, 2005, which is hereby incorporated by reference in its entirety.

FIELD OF THE INVENTION

The present invention relates to a carbon dioxide sensor comprising carbon dioxide-sensitive material attached to the electrodes of an electrical measuring device.

BACKGROUND OF THE INVENTION

Semiconductor gas sensors function by offering a change in electrical resistance in response to a shift in the local concentration of the gas of interest. In general the resistance of the sensor is some function of the concentration of the target gas. A major aim is to engineer a response, which is selective for a particular gas, without interference from other components of the atmosphere, including moisture (relative humidity).

Two general mechanisms are invoked to explain this concentration dependence on gas composition:

The mechanism operating at lower temperatures (generally within the range 200-500 C) involves reactions of the molecules of the target gas with chemisorbed species on the surface of the semiconductor, which is usually a metal oxide, and results in a change in near-surface charge carrier density. Examples of materials functioning through this mechanism can be employed in the detection and monitoring of either reducing gases (hydrogen, carbon monoxide, methane etc.) or oxidizing gases (nitrogen dioxide, chlorine, ozone etc.) in an air ambient. This response mechanism involves no change in the bulk composition of the semiconducting oxide.

Within a somewhat higher temperature range (approximately 500-700 C) a family of semiconducting oxides $MO_x$, where M represents either a transition metal or a combination of metals, one of which is a transition metal, can be used for monitoring oxygen partial pressure. In this case the bulk stoichiometry does change, because the oxygen content of the material (the value of x) equilibrates with the prevailing oxygen partial pressure. The change in x is compensated by a change in the ratio of the valence states of the transition metal component of M, and once again the charge carrier density changes.

The carbon dioxide molecule does not engage in reactions equivalent to those of either the reducing gases or the oxidizing gases such as those equivalent to those of mentioned above, and heretofore no useful semiconductor sensor for carbon dioxide has been described.

Needs exist for new carbon dioxide sensors.

SUMMARY OF THE INVENTION

It has now been discovered that a semiconductor gas sensor with a porous active material layer including an oxide with a surface that reacts with carbon dioxide can be used to detect carbon dioxide. The sensor of the present invention responds sensitively to low concentrations of carbon dioxide in an atmosphere of air. The carbonate species formed on the surface of the preferred oxides when they are exposed to carbon dioxide can be decomposed by raising the temperature, thus reforming the original oxide. A $CO_2$ sensor operating according to this principle may be cycled between the temperature at which the surface carbonate is decomposed and the temperature at which the surface carbonate is formed from atmospheric carbon dioxide.

The present invention relates to sensors and more particularly to sensors suitable for use in gaseous mixtures containing carbon dioxide.

In a preferred embodiment, a sensor is provided that is suitable for use in a gas or gaseous mixture. The sensor includes a carbon dioxide-sensitive material capable of exhibiting a response in the form of an increase or a decrease in an electrical property of the material in the presence of carbon dioxide.

In another preferred embodiment, the carbon dioxide-sensitive material is provided with two or more electrodes in communication with the carbon dioxide-sensitive material, and the carbon dioxide-sensitive material is arranged so as to be capable of being contacted with a carbon dioxide gas or gaseous mixture.

A sensor in accordance with the present invention may be used as a gas sensor in quantitative and/or qualitative determinations of carbon dioxide in gaseous mixtures. The electrodes may be in direct communication with the carbon dioxide-sensitive material by being in contact therewith.

The resistance and/or capacitance and/or impedance of the carbon dioxide-sensitive material depends upon the composition of the gaseous mixture contacting the carbon dioxide-sensitive material. Thus, by measuring the resistance and/or capacitance and/or impedance of the carbon dioxide-sensitive material the concentration of carbon dioxide in the gaseous mixture can be sensed.

Since the resistance and/or capacitance and/or impedance of the carbon dioxide-sensitive material tends also to be temperature-dependent, the sensor also preferably includes a temperature sensing means. The sensor may also include a heating means to enable operating temperature to be adjusted and/or contaminants to be burnt off if required.

The resistance and/or conductance and/or impedance may be measured directly. Alternatively, the measurement may be carried out indirectly by incorporating the sensor in a feedback circuit of an oscillator such that the oscillator frequency varies with composition of the gas or gaseous mixture. Gas composition may then be determined using an electronic counter. The signal thus produced may be used to modulate a radio signal and thereby be transmitted over a distance (e.g. by telemetry or as a pulse train along an optical fiber).

The present sensor responds to carbon dioxide.

In one preferred embodiment of the present invention, the carbon dioxide-sensitive material has two or more electrodes in communication with said carbon dioxide-sensitive material, and the carbon dioxide-sensitive material and the electrodes are in contact with the same gas.

Preferably the carbon dioxide-sensitive material has porosity to give a satisfactory surface area for contact with the gas or gaseous mixture when in use.

The carbon dioxide-sensitive material, for example, may be prepared from an appropriate precursor, which can be thermally decomposed to form an oxide. The precursor may optionally be prepared by a gel process such as a sol-gel process or a gel precipitation process and may be heated to form an oxide powder.

The powder may be dried and calcined at a given temperature, depending upon the particular composition of carbon dioxide-sensitive material being prepared. The product resulting from calcination, which may be in the form of a cake, may be ground as required to give a fine powder. If required, grinding and calcination may be repeated several times in order to obtain a more suitable powder.

Subsequently, the fine powder may be pressed (e.g. with the optional addition of a binder, such as a solution of starch or polyvinyl alcohol) into any suitable shape (e.g. a pellet).

A firing may follow the pressing (e.g. at the same temperature as the calcination step(s) described above, or at a somewhat higher temperature).

In addition to assisting in the binding of the powder into desired shapes, the binder also burns out during the firing stage, giving rise to porosity.

As an alternative a powder for subsequent calcination may be prepared, for example, by spray drying a solution (e.g. an aqueous solution) of appropriate starting material.

Electrodes may be applied to the prepared carbon dioxide-sensitive material in any suitable manner. For example, electrodes (e.g. gold electrodes) may be applied by means of screen printing or sputtering.

Alternatively to preparing a sensor by forming a pellet and applying electrodes as disclosed above, a sensor in accordance with the present invention may be formed in any suitable manner. Thus, for example, a parallel plate configuration may be fabricated by applying a first electrode (e.g. of gold) to an insulating substrate (e.g. by screen printing or sputtering), forming a carbon dioxide-sensitive material layer covering at least a portion of the first electrode (e.g. by deposition, for example by screen printing or doctor blading from a suspension or a colloidal dispersion and firing to promote adhesion and mechanical integrity) and forming a second electrode (e.g. of gold) on the carbon dioxide-sensitive material layer (e.g. by screen printing or sputtering). If the carbon dioxide-sensitive material is not stable within the temperature range required to promote adhesion and mechanical integrity (e.g. for silver oxide), then the carbon dioxide-sensitive material may be deposited as a thin layer on the surface of a porous material that is stable in the required temperature range, which can act as a host structure.

The second electrode is preferably permeable to facilitate access of gas or gaseous mixture, in which the sensor is to be used, to the carbon dioxide-sensitive material layer.

By way of further example, a coplanar configuration may be used in the preparation of a sensor in accordance with the present invention.

In such a coplanar configuration, interdigitated electrodes (e.g. of gold) may be formed on an insulating substrate (e.g. by screen printing or by sputtering or by photolithography and etching). The interdigitated electrodes are subsequently covered with a carbon dioxide-sensitive material layer (e.g. by means of deposition, for example by screen printing or doctor blading, from a suspension or a colloidal dispersion) and firing to promote adhesion and mechanical integrity.

The carbon dioxide-sensitive material disclosed by the present invention includes any one of a number of oxides that react with carbon dioxide in the atmosphere at one temperature and that can be reformed to oxide at a higher temperature, for example, zinc oxide, silver oxide, and metal tungstates such as potassium tungstate, and $K_2WO_4$.

These and further and other objects and features of the invention are apparent in the disclosure, which includes the above and ongoing written specification, with the drawings.

DETAILED DESCRIPTION OF THE PREFERRED EMBODIMENTS

Figure 1:
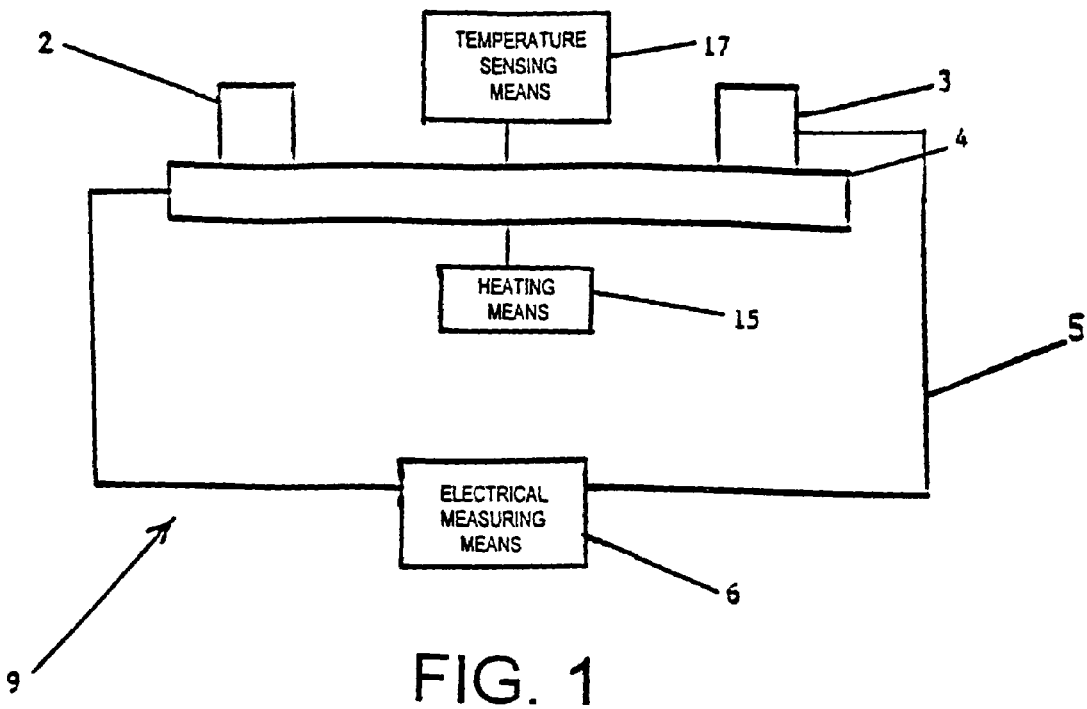
FIG. 1 is a diagrammatic representation of one form of a sensor in accordance with the present invention.

FIG. 1 shows a sensor 9 comprising a carbon dioxide-sensitive material 4 and, in contact with the carbon dioxide-sensitive material, gold electrodes 2 and 3. The carbon dioxide-sensitive material may be carried by a substrate (e.g. of alumina) (not shown).

Conductors 5 are provided to connect the electrodes 2 and 3 respectively to electrical measuring means 6 for measuring the resistance and/or capacitance and/or impedance of the carbon dioxide-sensitive material 4.

In operation a gas or gaseous mixture is contacted with the carbon dioxide-sensitive material 4.

The resistance and/or conductance and/or impedance is measured by the electrical measuring means 6. Changes in the carbon dioxide concentration of the gas or gaseous mixture that result in a change of resistance and/or conductance and/or capacitance and/or impedance are observed as changes in the resistance and/or conductance and/or capacitance and/or impedance recorded by the measuring means 6. Sensor 9 may include temperature sensing means 17 for sensing temperature and heating means 15 for heating the sensor.

Figure 2:
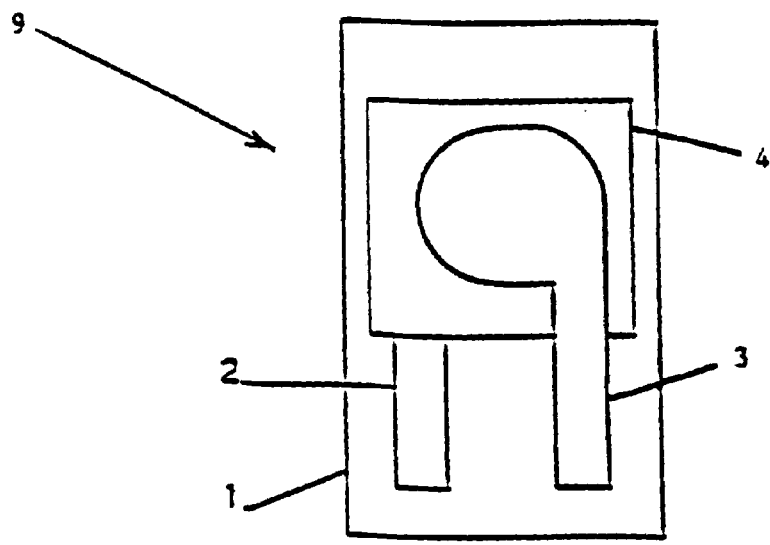
FIGS. 2 and 3 represent diagrammatically a parallel plate sensor in accordance with the present invention and a partially completed parallel plate sensor respectively.

FIG. 2 shows an insulating substrate 1 (e.g. an alumina ceramic tile) upon which is formed a first electrode 2 (e.g. of gold), a carbon dioxide-sensitive material layer 4 comprising a carbon dioxide-sensitive material in accordance with the present invention and a second electrode 3 (e.g. of gold).

A parallel plate sensor 9, as shown in FIG. 2, may be fabricated by applying the first electrode 2 (e.g. of gold) to the insulating substrate 1 (e.g. by screen printing or sputtering), forming a carbon dioxide-sensitive material layer 4 by deposition, for example by screen printing or doctor blading, from a suspension or a colloidal dispersion and firing to promote adhesion and mechanical integrity.

Figure 3:
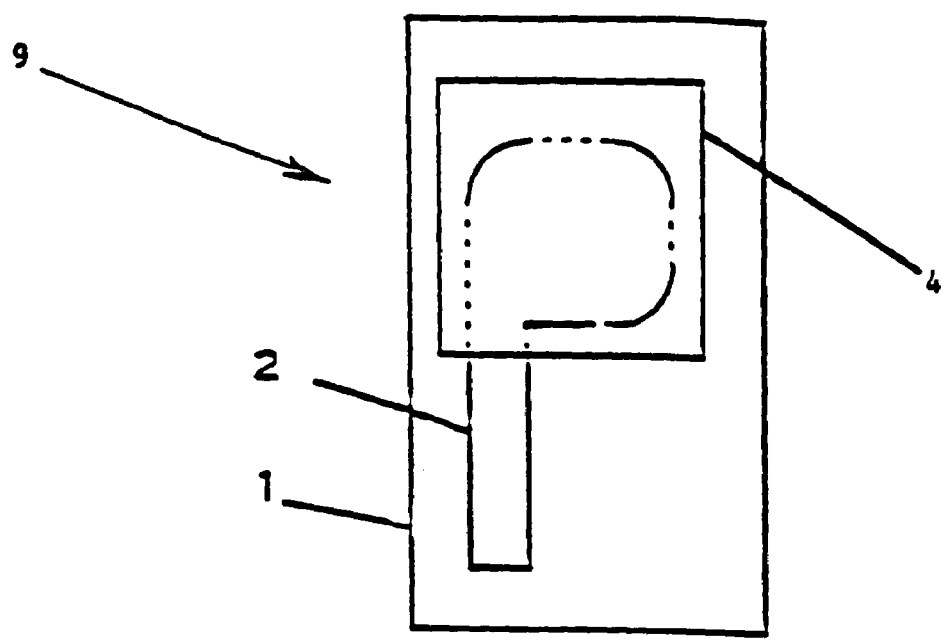

In order to facilitate understanding of the construction of the sensor of FIG. 2 reference may be made to FIG. 3, which shows a parallel plate sensor 9 of the type shown in FIG. 2 partially completed inasmuch as the second electrode 3 has not been formed. FIG. 3 thus shows the insulating substrate 1, the first electrode 2 and the carbon dioxide-sensitive material layer 4 and it is seen that the portion of the first electrode 2 covered by the carbon dioxide-sensitive material layer 4 may preferably extend in area to substantially the same extent as the second electrode 3.

In operation, the first electrode 2 and second electrode 3 are connected to an electrical measuring means (not shown) for measuring the resistance and/or capacitance and/or impedance of the carbon dioxide-sensitive material layer 4 and the sensor is contacted with a gas or gaseous mixture. The resistance and/or capacitance and/or impedance is measured by the electrical measuring means and changes in the carbon dioxide concentration of the gas or gaseous mixture which result in a change of resistance and/or capacitance and/or impedance are observed as changes in the resistance and/or capacitance and/or impedance recorded by the electrical measuring means.

Figure 4:
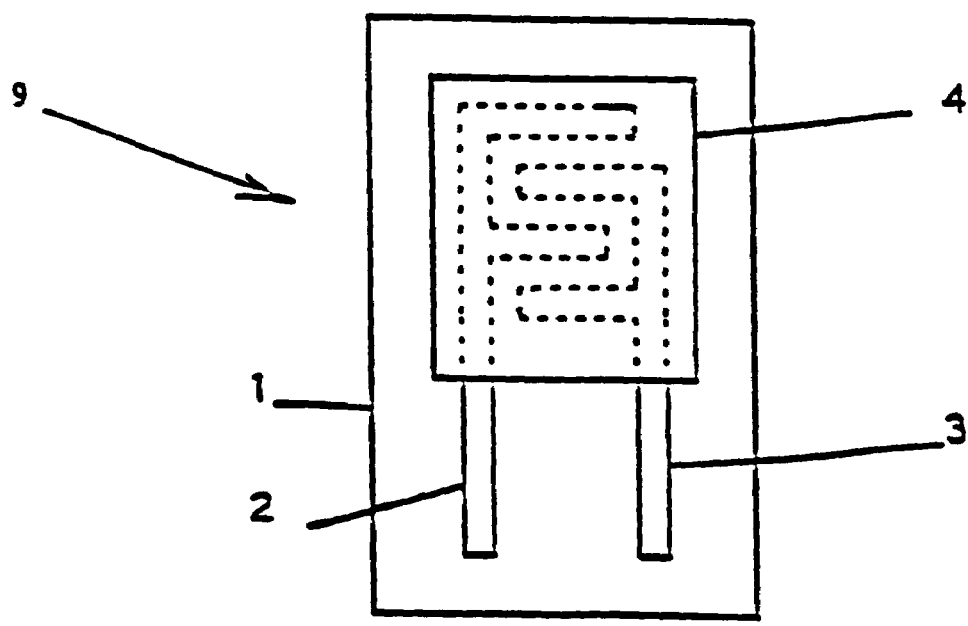
FIG. 4 is a diagrammatic representation of a coplanar sensor in accordance with the present invention.

FIG. 4 shows an insulating substrate 1 (e.g. an alumina ceramic tile upon which are formed electrodes 2 and 3 (e.g. both of gold), and a carbon dioxide-sensitive material layer 4 comprising a carbon dioxide-sensitive material in accordance with the present invention. It is seen from the lines shown in dotted form in FIG. 4 that the portions of the first electrode 2 and second electrode 3 covered by the carbon dioxide-sensitive material layer 4 are interdigitated.

The first electrode 2 and the second electrode 3 may be provided on the insulating substrate 1 by any suitable method. For example, the methods disclosed for providing electrodes 2 and 3 in the parallel plate sensor, described with reference to FIG. 2 and FIG. 3, may be used.

The carbon dioxide-sensitive material layer 4 shown in FIG. 4 may be prepared by any suitable method. For example, the methods disclosed for preparing carbon dioxide-sensitive material layer 4 in FIG. 2 and FIG. 3 may be used.

Sensors composed of a porous layer of potassium tungstate or of zinc oxide are useful for the detection of carbon dioxide.

EXAMPLE 1

Figure 5:
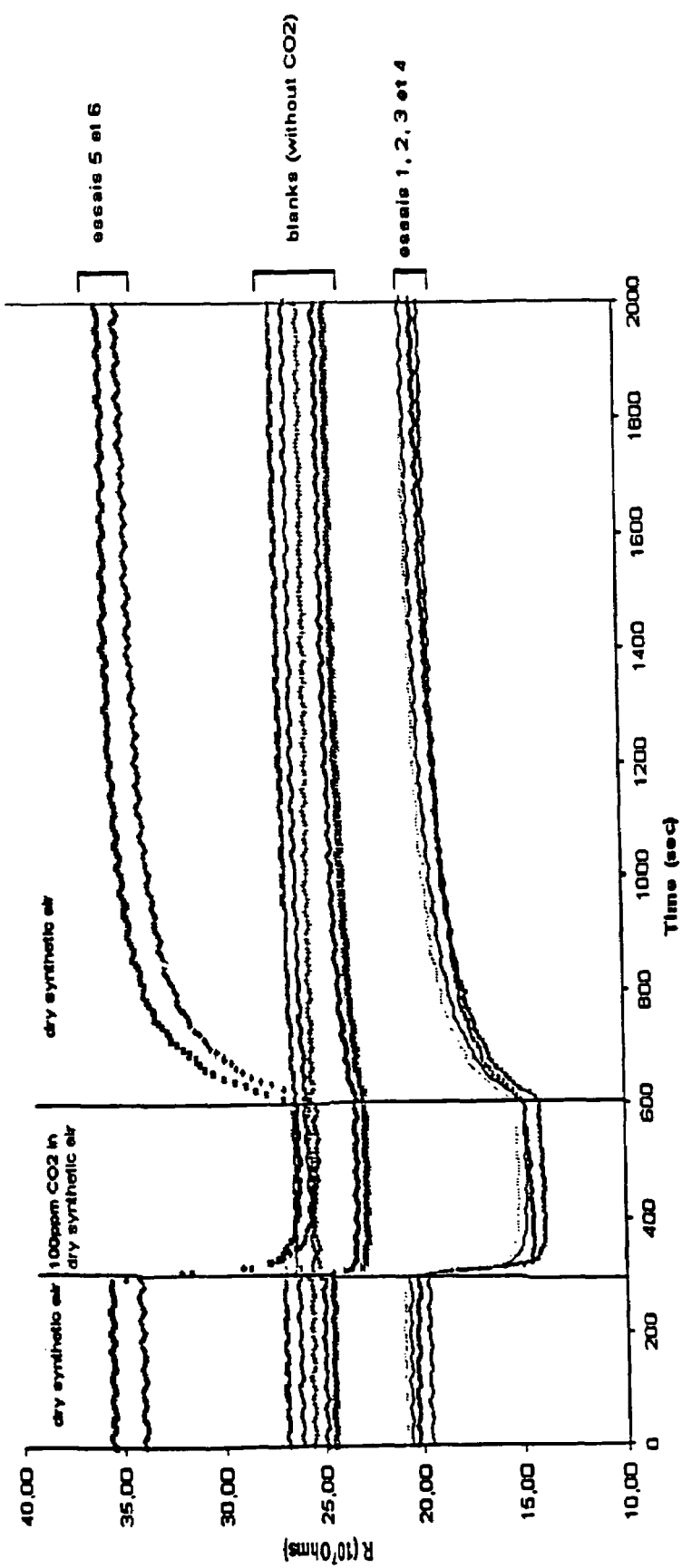
FIG. 5 is a graph of a response of a potassium tungstate sensor to a pulse of 100 ppm of carbon dioxide in an atmosphere of dry air.

A layer of 100 mesh potassium tungstate some 30 microns thick was screen printed over a pair of interdigitated electrodes on an alumina substrate and the operating temperature was controlled by means of a platinum resistance heater printed on the reverse side of the substrate. FIG. 5 shows the response of the sensor to the introduction of a pulse of 100 parts per million of carbon dioxide to an atmosphere of dry air.

The resistance decrease in the presence of $CO_2$, shown in FIG. 5, is due to the reaction:

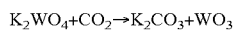

$$K_2WO_4 + CO_2 \rightarrow K_2CO_3 + WO_3$$

That reaction forms tungsten trioxide that has a higher conductivity than potassium tungstate.

EXAMPLE 2

Silver oxide ($Ag_2O$), zinc oxide or a mixture of the two is suggested as $CO_2$ chemisorbent in systems for removing carbon dioxide from atmospheres in deep space life support equipment. These systems can be adapted to function as $CO_2$ detectors.

An insulating substrate has a Pt resistance heater printed on one surface and a set of interdigitated electrodes overlaid with a porous coating of the oxide ($Ag_2O$, ZnO or a mixture of the two) on the other.

The heater is used to raise the temperature above the surface carbonate decomposition temperature and then the temperature can be dropped to a level where any $CO_2$ in the atmosphere adsorbs on the oxide surface. The amount of $CO_2$ in the atmosphere is reflected in the rate at which the resistance of the oxide layer changes after the reduction in temperature and by the final value reached by the resistance. The device may be used in a temperature cycling mode.

The sensitivity of the system depends inversely on the size of the particles in a porous oxide layer or the thickness of a dense layer.

Figure 6:
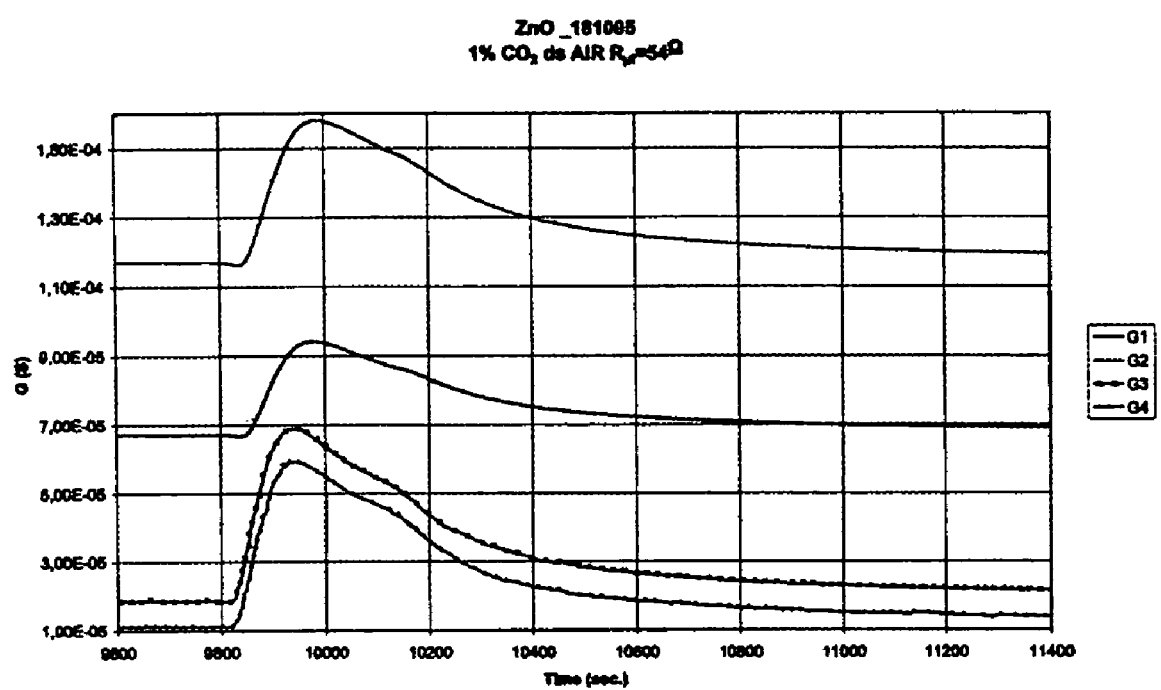
FIG. 6 shows the responses of 4 zinc oxide sensors to the introduction of a pulse of 1% $CO_2$ (between times 9800 and 10100 seconds) in an atmosphere of dry air.

The resistance change of a zinc oxide sensor exposed to a pulse of 1% $CO_2$ in dry air is shown in FIG. 6.

While the invention has been described with reference to specific embodiments, modifications and variations of the invention may be constructed without departing from the scope of the invention.

We claim:

1. A method of sensing carbon dioxide, comprising providing an alumina substrate, providing a spaced pair of interdigitated electrodes on one side of the alumina substrate, providing a platinum resistance heater on a reverse side of the substrate, printing a layer potassium tungstate mesh over the pair of interdigitated electrodes, heating the substrate to a temperature in which carbon dioxide is attracted to the potassium tungstate mesh, reacting carbon dioxide with the potassium tungstate and forming tungsten trioxide, measuring resistance of tungsten trioxide between the electrodes and sensing carbon dioxide in an atmosphere of dry air.

2. The method of claim 1, wherein the printing a layer comprises printing a layer of potassium tungstate of about 100 mesh about 30 microns thick, and the sensing carbon dioxide at a concentration of about 100 parts per million of carbon dioxide.

* * * * *

UNITED STATES PATENT AND TRADEMARK OFFICE
CERTIFICATE OF CORRECTION

PATENT NO. : 7,628,957 B1 Page 1 of 1
APPLICATION NO. : 11/475839
DATED : December 8, 2009
INVENTOR(S) : Patrick T. Moseley, Odile Merdrignac-Conanec and Ronan Lebullenger It is certified that error appears in the above-identified patent and that said Letters Patent is hereby corrected as shown below:

On the Title Page
Item (76) should read:

Inventors: Patrick T. Moseley, 2525 Meridian Pkwy, Durham, NC (US) 27713
Odile Merdrignac-Conanec, 2525 Meridian Pkwy, Durham, NC (US) 27713
Ronan Lebullenger, 2525 Meridian Pkwy, Durham, NC (US) 27713

Signed and Sealed this

Twenty-third Day of March, 2010

David J. Kappos
*Director of the United States Patent and Trademark Office*